(12) United States Patent
Heesch et al.

(10) Patent No.: US 8,997,741 B2
(45) Date of Patent: Apr. 7, 2015

(54) RESPIRATION SYSTEM

(75) Inventors: Ralf Heesch, Lübeck (DE); Henryk Schnaars, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 579 days.

(21) Appl. No.: 13/359,821

(22) Filed: Jan. 27, 2012

(65) Prior Publication Data

US 2013/0025595 A1 Jan. 31, 2013

(30) Foreign Application Priority Data

Jun. 30, 2011 (EP) .................................. 11172088

(51) Int. Cl.
| | | |
|---|---|---|
| A61M 16/22 | (2006.01) | |
| A61M 16/08 | (2006.01) | |
| A61M 16/20 | (2006.01) | |
| A61M 16/10 | (2006.01) | |

(52) U.S. Cl.
CPC ......... *A61M 16/0816* (2013.01); *A61M 16/208* (2013.01); *A61M 16/0833* (2014.02); *A61M 16/0891* (2014.02); *A61M 16/209* (2014.02); *A61M 16/104* (2013.01); *A61M 16/22* (2013.01)

(58) Field of Classification Search
CPC .......... A61M 16/208; A61M 16/0816; A61M 16/209; A61M 16/0833; A61M 16/0891; A61M 16/104; A61M 16/085; A61M 16/01; A61M 16/1015; A61M 16/202; A61M 16/18; A61M 16/0081; A61M 16/20; A61M 16/205; A61M 16/22
USPC ............. 128/203.28, 203.14, 203.12, 205.24, 128/204.21, 200.24, 203.25, 203.16, 205.11
See application file for complete search history.

(56) References Cited

U.S. PATENT DOCUMENTS

| | | | | |
|---|---|---|---|---|
| 3,578,019 | A * | 5/1971 | Turolla | 137/491 |
| 4,207,884 | A | 6/1980 | Isaacson | |
| 4,966,183 | A * | 10/1990 | Williamson, Jr. | 137/116.5 |
| 7,726,307 | B2 * | 6/2010 | Dittmann et al. | 128/203.14 |
| 8,176,914 | B2 * | 5/2012 | Zhang et al. | 128/203.12 |
| 8,627,817 | B2 * | 1/2014 | Heesch | 128/203.12 |
| 2009/0277448 | A1 * | 11/2009 | Ahlmen et al. | 128/204.21 |
| 2010/0252046 | A1 * | 10/2010 | Dahlstrom et al. | 128/205.24 |
| 2011/0000488 | A1 * | 1/2011 | Blomberg | 128/203.14 |

FOREIGN PATENT DOCUMENTS

| | | |
|---|---|---|
| DE | 10041007 C1 | 9/2001 |
| DE | 102004052398 B3 | 11/2005 |
| EP | 0894506 B1 | 12/2004 |

*Primary Examiner* — Annette Dixon
(74) *Attorney, Agent, or Firm* — McGlew and Tuttle, P.C.

\* cited by examiner

(57) ABSTRACT

A respiration system feeds an anesthetic gas having, a density $\rho_{gas}$, with a Y-piece for connection to a patient, with a respiration circuit having an inspiration branch and an expiration branch, which extend away from the Y-piece. A first supply line from a branch in the expiration branch leads to an anesthetic gas discharge valve and a second supply line from the branch leads to a reservoir. A too high pressure, opposing expiration, cannot build up in the expiration branch and losses of anesthetic gas are kept to a minimum. A prestressing device exerts a prestressing force onto the valve body of the anesthetic gas discharge valve against the effect of gravity. The mass $m_{valve}$ and the prestressing force determine a threshold pressure in the anesthetic gas discharge line that results in an opening of the anesthetic gas discharge valve.

20 Claims, 2 Drawing Sheets

1

RESPIRATION SYSTEM

CROSS REFERENCE TO RELATED APPLICATIONS

This application claims the benefit of priority under 35 U.S.C. §119 of European Application EP 11 172 088.4 filed Jun. 30, 2011, the entire contents of which are incorporated herein by reference.

FIELD OF THE INVENTION

The present invention pertains to a respiration system for feeding an anesthetic gas with a Y-piece, which is provided for connection to a patient, with a respiration circuit, in which are provided an inspiration branch and an expiration branch, which extend away from the Y-piece, whereby a branching is provided in the expiration branch, whereby a first supply line from the branching leads to an anesthetic gas discharge valve and whereby a second supply line from the branching leads to a reservoir.

BACKGROUND OF THE INVENTION

Such respiration systems known from the state of the art, for example, EP 0 894 506 B1, first have the advantage that the anesthetic gas is guided in a respiration circuit, so that a large part of the expensive anesthetic gas can be reused. Only $CO_2$ has to be removed from the circulating gas flow by means of an absorber, and the oxygen concentration has to be kept at a preset level.

By means of the manual respiration bag which is likewise contained in the circuit, it is possible for an anesthesiologist to manually adjust the pressure operating during the inspiration and the duration of the inspiration.

However, the following problem arises in such systems. During expiration, resistance or pressure opposing the expiration should not exceed a certain value, whereby, especially at the end of the expiration cycle, the pressure in the expiration branch may rise, for example, when the capacity of the reservoir is not sufficient. So that this resistance does not become unacceptably high, a so-called anesthetic gas discharge valve (hereinafter "NGF valve"), which opens in case of an excess pressure in the expiration branch of 1.2±0.1 mbar, is provided in the expiration branch. In the state of the art, this valve is usually designed, such that a valve body is pressed against a valve seat by means of a spring, whereby the prestress of the spring determines the threshold, at which the valve opens.

The flow in the expiration branch, especially at the beginning of expiration, is not constant, and also the pressure, which builds up during expiration at the NGF valve, fluctuates and has brief peaks or large pressure gradients in the range of $$\frac{\Delta p}{\Delta t} = \frac{5\text{mbar}}{0.5\text{ sec}},$$

so that pressures briefly lying above the above-mentioned threshold at the NGF valve build up, which consequently bring about the situation that the gas in the supply line to the manual respiration bag has an inertia. On top of that, the NGF valve also briefly opens, although a pressure above the threshold has not built up for a longer period in the expiration branch. Thus, a so-called "rattling" of the NGF valve occurs, which leads to an unnecessary loss of anesthetic gas.

SUMMARY OF THE INVENTION

Therefore, based on the above-described state of the art, an object of the present invention is to provide a respiration system, in which too high pressure opposing the expiration cannot build up in the expiration branch and which nevertheless keeps the losses of anesthetic gas to a minimum.

This object is accomplished by a respiration system for feeding an anesthetic gas having a density $\rho_{Gas}$, with a Y-piece, which is provided for connection to a patient, with a respiration circuit, in which an inspiration branch and an expiration branch are provided, which extend away from the Y-piece, whereby a branching is provided in the expiration branch, whereby a first supply line from the branching leads to an NGF valve, whereby a second supply line from the branching leads to a reservoir, which has a mean cross-sectional area $A_{supply\ line\ 2}$ and a length $l_{supply\ line\ 2}$, whereby the NGF valve has a valve body with a mass $m_{valve}$, which is pressed, by the effect of gravity, towards the first supply line against a circular-ring-shaped valve seat having a diameter $d_{valve}$, and whereby a prestressing means is provided, which exerts a prestressing force onto the valve body against the effect of gravity, so that the mass $m_{valve}$ and the prestressing force determine a threshold pressure $\Delta P_{threshold}$, about which the pressure in the first supply line has to lie at least above that on the side of the anesthetic gas discharge valve facing away from the first supply line, so that this opens.

In conventional NGF valves known from the state of the art, the valve body is pressed against the valve seat by means of a prestressing means, such as a spring, whereby the spring force and the weight of the valve body acting in the same direction together determine the threshold pressure, at which the valve opens. Since the threshold pressure has to be very low, however, the weight and the spring force may also not be very high.

In the solution according to the present invention, a part of the gravity, which acts on the valve body and based on which the valve closes, is compensated by means of the prestressing means which acts against the direction of gravity. This makes it possible that the valve body may have a markedly greater mass and thus may be inactive in situations, so that only brief pressure peaks or preferably high pressure gradients of approximately $$\frac{\Delta p}{\Delta t} = \frac{5\text{mbar}}{0.5\text{ sec}}$$

and thus only a brief force action are not sufficient to raise the valve body from the valve seat. Therefore, the mass of the valve body as well as the density $\rho_{gas}$ of the anesthetic gas used can be adapted to the remaining parts of the respiration system to achieve the inertia of the valve needed based on the design of the respiration system.

The adaptation is especially done depending on the length of the second supply line to the reservoir and on the cross section of this supply line as well as on the driving pressure of the patient, such that the pressure gradients in the supply line to the reservoir are not sufficient at the NGF valve to move the valve body thereof from its closed position, in which it lies against the valve seat. Consequently, the NGF valve opens only if a pressure, whose difference to the ambient pressure lies above the threshold pressure $\Delta P_{threshold}$, builds up in the expiration branch for a longer period, so that the loss of anesthetic gas is minimized.

Preferably, the mass $m_{valve}$ of the valve body is selected in such a way that $$m_{valve} > \frac{\sqrt{2} \cdot \pi^2 \cdot l_{supplyline2}^2 \cdot \dot{V}_{intersection} \cdot \rho_{gas}^2 \cdot d_{valve}^3 \cdot (\Delta P - \Delta P_{threshold})}{8 \cdot A_{supplyline2}^2 \cdot \Delta P^2 \cdot \sqrt{\frac{\rho_{gas}}{\Delta P}}}$$

applies, whereby the parameter $\dot{V}_{intersection}$ is selected corresponding to $\dot{V}_{intersection} \geq 10$ L/min and $\Delta P = 5$ mbar is assumed for the driving pressure $\Delta P$ during the expiration of the patient. $\Delta P_{threshold} = 1.1$ mbar is selected for the threshold pressure, and the density $\rho_{gas}$ of the anesthetic gas lies between 1.12 kg/m³ and 2.19 kg/m³. A breathing gas temperature of 20° C. is used as the basis here. When the density of the breathing gas is established, which shall be used in the system, the corresponding value for the density in Equation (1) can be used to thus adapt the system accordingly, whereby this density value lies within the interval defined above.

Thus, a specification is given by Equation (1) for dimensioning the valve body depending on the other relevant dimensions within the respiration system. When this specification is complied with, it is reliably guaranteed that the NGF valve does not already open at brief high pressure gradients in the range of $$\frac{\Delta p}{\Delta t} = \frac{5 \text{ mbar}}{0.5 \text{ sec}}$$

based on the adequate inertia of the valve body, which pressure gradients result from the flow resistance in the second line to the reservoir or manual respiration bag and the inertia of the gas present therein. Rather, the NGF valve opens only if the pressure in the expiration branch lies about the threshold pressure above the ambient pressure for a longer time.

Such pressure gradients appear cyclically during the respiration operation due to a continual change between inspiration and expiration of the patient, whereby the inertia of the gas in the supply line to the reservoir leads to pressure gradients building up precisely in the supply line to the NGF valve. The respiration rate and thus the frequency of such peaks lies within the range of 6 to 15 breaths per minute in a typical patient.

Equation (1) is based on the following marginal conditions and considerations.

It is assumed that during expiration based on the driving pressure $\Delta P$ of the patient, anesthetic gas flows along the expiration branch, in particular both along the first supply line to the NGF valve and along the second supply line to the reservoir or to the manual respiration bag. For the inertia $I_{pneu}$ of the gas in the second supply line, $$I_{pneu} = \frac{\Delta P}{\left(\frac{d}{dt}\dot{V}\right)} = \frac{\rho_{gas} \cdot l_{supplyline2}}{A_{supplyline2}}, \quad (2)$$

applies, whereby a supply line with an essentially circular cross section is assumed. Moreover, for the inertia of the NGF valve, $$I_{NGF} = \frac{2 \cdot m_{valvebody}}{\pi^2 \cdot d_{valve}^3} \cdot \sqrt{\frac{2 \cdot \rho_{gas}}{\Delta P}}, \quad (3)$$

applies, whereby a circular valve seat having a diameter $d_{valve}$ is assumed. The valve seat is that surface area, on which the valve body lies against the valve housing. Thus, the volume flow can be calculated as a function of the time t through the second supply line to the reservoir via the equation $$\dot{V}_{supplyline2} = \frac{t \cdot \Delta P}{I_{pneu}}, \quad (4)$$

while for the time curve of the volume flow through the NGF valve $$\dot{V}_{NGF} = \frac{1}{2} \cdot t^2 \frac{\Delta P - \Delta P_{threshold}}{I_{pneu}}, \quad (5)$$

applies. This means that the volume flow $\dot{V}_{supply\,line\,2}$ through the second supply line to the reservoir or manual respiration bag increases linearly with time, while the volume flow $\dot{V}_{NGF}$ through the NGF valve has a square course.

This arises due to the fact that volume flow $\dot{V}_{supply\,line\,2}$ into the reservoir at constant driving pressure $\Delta P$ is proportional to time t, while volume flow $\dot{V}_{NGF}$ through the NGF valve is proportional to the size of the gap between valve body and valve seat. This is in turn increased by the movement of the valve body, whereby the acceleration of the valve body is proportional to the force that is exerted on it. This is in turn proportional to the driving pressure $\Delta P$. When this is constant, there is a constant acceleration and the size of the gap is proportional to the time squared $t^2$.

Now, for the dimensioning of the respiration system, it is required that the volume flow $\dot{V}_{NGF}$ through the NGF valve shall exceed the volume flow through the supply line only after a relatively long time and not already at the above-defined high pressure gradients. The NGF valve shall thus open only very slowly, which means that the intersection $\dot{V}_{intersection}$ between the two volume flows $\dot{V}_{supply\,line\,2}$ and $\dot{V}_{NGF}$ has to lie first at a point in time $t_{intersection}$, which is greater than the duration of the pressure gradients occurring, or at a relatively high volume flow.

When Equations (4) and (5) are compared to determine the intersection $\dot{V}_{intersection}$ and Equations (2) and (3) are used for the inertias, at first a relationship arises for $t_{intersection}$. Thus, the relationship $$\dot{V}_{intersection} = \frac{4 \cdot A_{supplyline2} \cdot m_{valve} \cdot \Delta P^2 \sqrt{\frac{2 \cdot \rho_{gas}}{\Delta P}}}{\pi^2 \cdot l_{supplyline2}^2 \cdot \rho_{gas}^2 \cdot d_{valve}^3 \cdot (\Delta P - \Delta P_{threshold})}, \quad (6)$$

can be established by using the intersection time $t_{intersection}$ in Equation (4) together with Equation (2).

The condition for the mass of the valve body $M_{valve}$ according to Equation (1) in turn arises from this by transposing. In this case, the relationship $\dot{V}_{intersection} \geq 10$ L/min, and preferably $\dot{V}_{intersection} \geq 60$ L/min should apply for $\dot{V}_{intersection}$.

If $\dot{V}_{intersection} \geq 10$ L/min is selected, a significant effect is already produced especially in the area of pediatrics. A value of $\dot{V}_{intersection} \geq 60$ L/min is adjusted to an adult and corresponds approximately to the peak volume flow that an adult can achieve.

While previously circular cross sections of the supply lines were used as the starting point, it is clear that variations with noncircular cross sections are also comprised by the present invention.

In a preferred embodiment, the NGF valve is designed in such a way that it has a valve housing, in which the valve seat is provided, whereby the valve seat runs in a seat plane running at right angles to the direction of gravity and points in a direction opposite the direction of gravity, and whereby the valve body is arranged in such a way that it lies on the valve seat under the effect of gravity.

It is further preferred, when a screw spring is provided as prestressing means, which lies with a first end against the valve body, which presses on the valve body against the effect of gravity and which is arranged on the side of the valve body pointing in the direction of gravity.

To be able to adjust the prestressing by means of the spring and thus the threshold pressure ΔP in a simple manner, it is further preferred that an adjusting screw is axially adjustably mounted in the valve housing, whereby the second end of the screw spring is supported against the adjusting screw.

The present invention is explained below based on a drawing showing only one preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
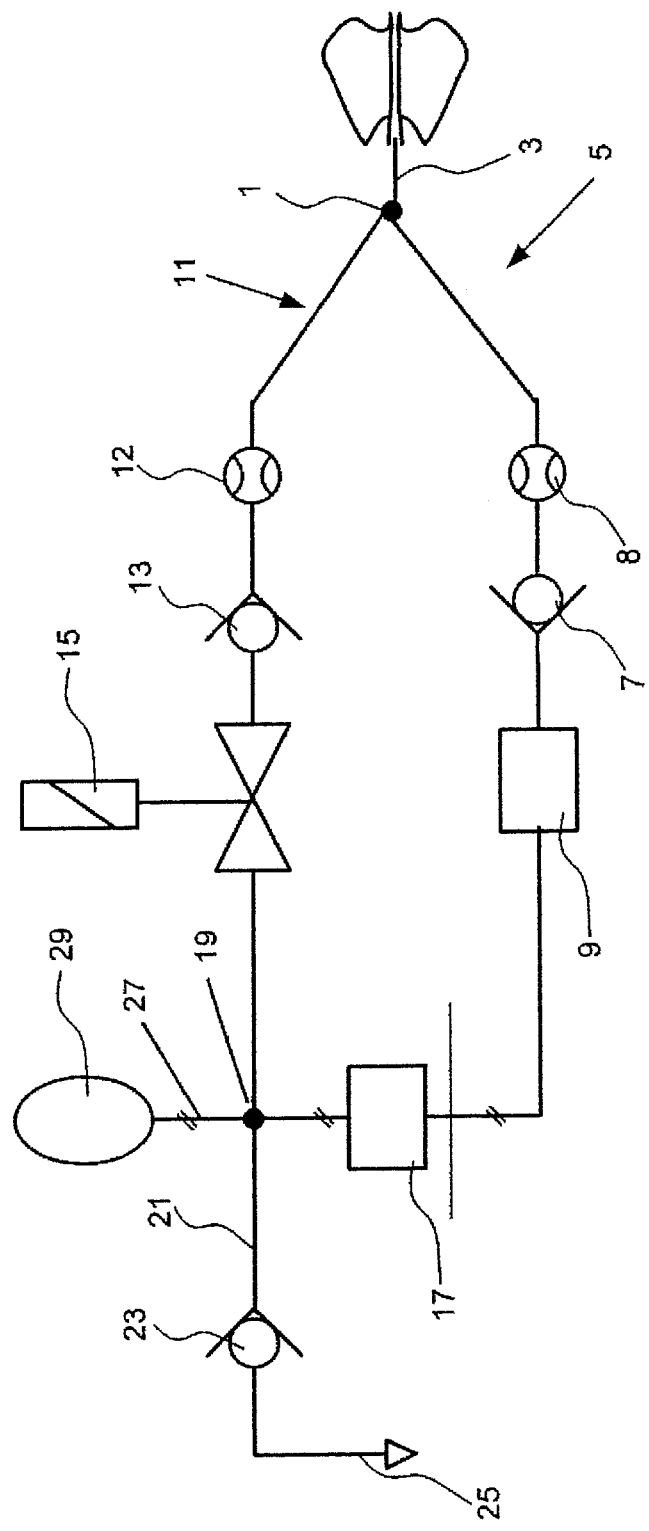
FIG. 1 is a schematic view of the exemplary embodiment of a respiration system according to the present invention.

Referring to the drawings in particular, the exemplary embodiment of a respiration system shown in FIG. 1 comprises a respiration circuit (shown only schematically here) with a Y-piece 1, from which a connection line 3 originates, via which a patient can be connected to the respiration system. The respiration circuit further comprises an inspiration branch 5 originating from the Y-piece 1, in which a first nonreturn valve 7, a first measuring means 8 for measuring the volume flow in the inspiration branch 5 as well as a ventilation and gas dispensing device 9 are provided.

The nonreturn valve 7 is designed here such that only a flow from the ventilation and gas dispensing device 9 towards the Y-piece 1 can take place in the inspiration branch 5, while the first nonreturn valve 7 closes in case of a flow running in the reverse direction. A respiration drive, with which a flow can be brought about to the Y-piece 1 and thus to the patient, as well as a fresh gas dispensing means are present in the ventilation and gas dispensing device 9.

Moreover, an expiration branch 11 originates from the Y-piece 1, in which a second measuring means 12, a second nonreturn valve 13 as well as a PEEP (PEEP corresponds to "positive end expiratory pressure") valve 15 are provided.

The second nonreturn valve 13 is arranged in such a way that a flow from the Y-piece 1 to the PEEP valve 15 is made possible, while the second nonreturn valve 13 closes in case of a flow in the reverse direction.

The functionality of the PEEP valve 15 is such that the PEEP valve 15 is closed during the inspiration phase, so that gas, which shall be fed from the ventilation and gas dispensing means 9 actually to the patient, cannot flow away via the expiration branch 11. In the expiration phase, the PEEP valve 15 is set in such a way that it maintains a positive pressure in the section between the PEEP valve 15 and the Y-piece 1.

Furthermore, the expiration branch 11 has a $CO_2$ absorber 17, whereby, viewed from the direction of the Y-piece 1, the expiration branch 11 and the inspiration branch 5 are connected to each other behind the $CO_2$ absorber 17.

Moreover, a branching 19, from which a first supply line 21 originates, at whose end an anesthetic gas discharge valve (hereinafter "NGF valve") 23 is arranged, is provided in the expiration branch 11. The output side of the NGF valve 23 is in turn connected to an anesthetic gas discharge system 25, not shown in detail.

Furthermore, a second supply line 27, which may have a comparatively long length $l_{supply\ line\ 2}$ of more than 1 m and extends to a manual respiration bag 29, which forms the reservoir in the present exemplary embodiment, originates from the branching 19. Due to this long length $l_{supply\ line2}$, the gas therein may also have a considerable inertia. The second supply line 27 has a cross-sectional area $A_{supply\ line\ 2}$. If the cross section of the second supply line 27 varies over its length, the inertias of the breathing gas would have to be calculated separately in sections each with a constant cross section (see above), whereby a relationship deviating from Equation (1) would arise. However, it is obvious to the person skilled in the art how the correspondingly transposed equation must appear.

With regard to the branching 19, it should be noted that both supply lines 21, 27 originate from one point in the expiration branch 11 in the present exemplary embodiment of the branching 19. However, it is conceivable as well that the branching 19 is split, so that the first and second supply lines 21, 27 originate from the expiration branch 11, spaced apart from one another.

Figure 2:
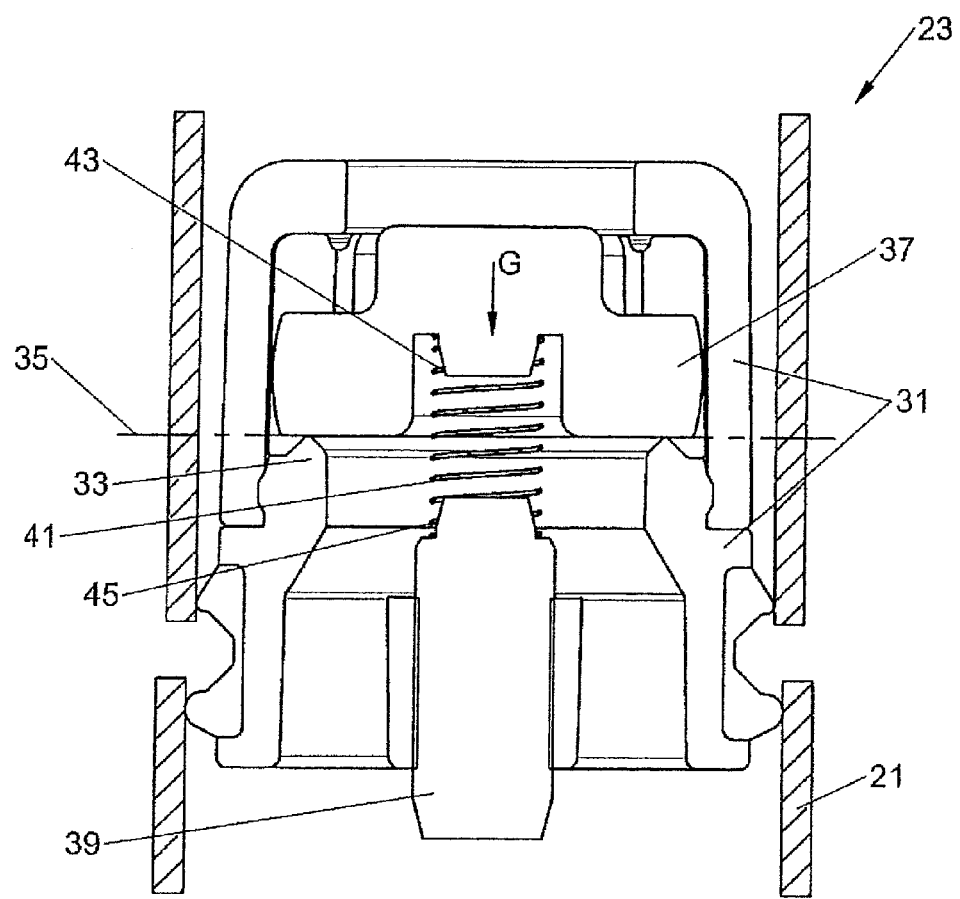
FIG. 2 is a sectional view of the anesthetic gas discharge valve used in the respiration system of FIG. 1.

FIG. 2 shows the NGF valve 23 in detail, and it can be seen that this NGF valve 23 has a housing 31 with a circular valve seat 33 arranged therein, which extends in a seat plane 35 which runs at right angles to the direction of gravity G, and has a diameter $d_{valve}$. Moreover, a mobile valve body 37, which has a mass $m_{valve}$ and lies on the valve seat 33 because of its weight and thus closes the valve 23, is provided in the housing 31. Finally, an adjusting screw 39 is arranged in the housing 31, whereby a screw spring 41 is arranged between the end of the adjusting screw 39 located in the housing interior and the valve body 37. The first end 43 of the screw spring is supported against the valve body 37, and the second end 45 lies against the adjusting screw 39. Thus, a part of the weight of the valve body 37 is compensated by the prestressing means in the form of the screw spring 41, such that the weight of the valve body 37, on the one hand, and the prestressing of the valve body 37, on the other hand, determine at what threshold pressure $\Delta P_{threshold}$ the NGF valve 23 opens, provided that this threshold pressure $\Delta P_{threshold}$ is exceeded by the pressure difference between the side of the NGF valve 23 that is facing the supply line 21 and the side that points to the anesthetic gas discharge system 25. Thus, this threshold pressure $\Delta P_{threshold}$ can be adjusted by adjusting the adjusting screw 39.

Finally, in this exemplary embodiment described above, the mass $m_{valve}$ of the valve body 37 is determined according to the equation $$m_{valve} > \frac{\sqrt{2} \cdot \pi^2 \cdot l_{supplyline2}^2 \cdot \dot{V}_{intersection} \cdot \rho_{gas}^2 \cdot d_{valve}^3 \cdot (\Delta P - \Delta P_{threshold})}{8 \cdot A_{supplyline2}^2 \cdot \Delta P^2 \cdot \sqrt{\frac{\rho_{gas}}{\Delta P}}} \quad (1)$$

already explained above, to embody the NGF valve 23 as being sufficiently inert, so that brief high pressure gradients do not already bring about an opening of the NGF valve 23.

The parameters contained in this equation describe, on the one hand, the dimensions of parts of the respiration system. Thus, the length of the second line 27 $l_{supply\ line\ 2}$, the diameter of the valve seat 31 $d_{valve}$, the threshold pressure $\Delta P_{threshold}$ adjusted at the NGF valve 23 (usually approximately 1.1 bar) and the cross-sectional area $A_{supply\ line\ 2}$ of the second supply line 27 appear in Equation (1). When the cross-sectional shape of the second supply line varies along the length thereof, Equation (1), as was already explained, has to be transposed accordingly in an obvious manner.

On the other hand, other parameters, which concern the respirated patient or the breathing gas used and are likewise readily known, appear. These [parameters] are the density of the breathing gas $\rho_{gas}$, which may lie between 1.12 kg/m$^3$ and 2.19 kg/m$^3$, so that a comparatively close range is preset here, the driving pressure $\Delta P$, which is generated by the patient breathing out and is 5 mbar, and the intersection volume flow $\dot{V}_{intersection}$, for which $\dot{V}_{intersection} \geq 10$ L/min and preferably $\dot{V}_{intersection} \geq 60$ L/min applies. The density of the breathing gas is determined by the composition of air, oxygen, nitrous oxide and volatile anesthetics in the gas mixture, whereby a breathing gas temperature of 20° C. is used as a basis.

Thus, the valve body can easily be determined by means of Equation (1), even if the anesthetic gas and thus its density are not determined accurately.

The respiration system described above operates as follows. In the inspiration phase, the respiration drive provided in the ventilation and gas dispensing means 9 is turned on, so that the first nonreturn valve 7 opens and the PEEP valve 15 is closed. Consequently, breathing gas, whose concentration is controlled by the ventilation and gas dispensing means 9, reaches the patient via the Y-piece 1 and the connection line 3, whereby a part of the breathing gas comes from the manual respiration bag 29.

During expiration, the first nonreturn valve 7 is closed because of the driving pressure $\Delta P$ which is generated by the patient and the second nonreturn valve 13 is opened, so that the expired gas flows along the expiration branch 11 through the PEEP valve 15 to the branching 19, whereby the PEEP valve 15 guarantees that the pressure, for example determined by the second measuring means 12, does not fall below a preset threshold.

The gas flows from the branching 19 along second supply line 27 into the manual respiration bag 29 until a pressure builds up in the expiration branch 11, which, compared to the ambient pressure, lies above the threshold pressure $\Delta P_{threshold}$ of the NGF valve 23. Only then can the NGF valve 23 open, whereby this cannot happen already beforehand due to brief pressure fluctuations or pressure gradients in the range of $$\frac{\Delta p}{\Delta t} = \frac{5\ \text{mbar}}{0.5\ \text{sec}},$$

since the opening behavior of the NGF valve 23 is sufficiently inactive (inert) because of the comparatively high mass $m_{valve}$ determined according to Equation (1).

In the next inspiration phase, gas again flows from the manual respiration bag 29 through the $CO_2$ absorber 17 back into the inspiration branch 5 and is possibly changed in its composition by means of the ventilation and gas dispensing means 9 and then fed to the patient via the Y-piece 1.

As emerges from the above, the respiration system according to the present invention is embodied by the NGF valve 23, whose valve body 37 is dimensioned corresponding to the conditions in the system, in such a way that the NGF valve 23 only opens if a pressure, whose difference to ambient pressure lies above the threshold pressure $\Delta P_{threshold}$, builds up in the expiration branch for a longer period, so that the loss of anesthetic gas is minimized.

While a specific embodiment of the invention has been shown and described in detail to illustrate the application of the principles of the invention, it will be understood that the invention may be embodied otherwise without departing from such principles.

What is claimed is:

1. A respiration system for feeding an anesthetic gas having a density $\rho_{gas}$, the system comprising:
   a Y-piece for connection to a patient;
   a respiration circuit with an inspiration branch and an expiration branch, which extend away from the Y-piece;
   a branching in the expiration branch;
   an anesthetic gas discharge valve;
   a first supply line connected from the branching and leading to the anesthetic gas discharge valve;
   a reservoir;
   a second supply line connected from the branching and leading to the reservoir, said second supply line having a cross-sectional area $A_{supply\ line\ 2}$ and a length $l_{supply\ line\ 2}$, wherein:
   the anesthetic gas discharge valve comprises a valve body having a mass which is pressed, by means of the effect of gravity, towards the first supply line against a circular-ring-shaped valve seat having a diameter; and
   the anesthetic gas discharge valve includes a prestressing means for exerting a prestressing force onto the valve body against the effect of gravity, so that the mass and the prestressing force determine a threshold pressure about which the pressure in the first supply line has to lie at least above that on the side of the anesthetic gas discharge valve facing away from the first supply line to open the anesthetic gas discharge valve.

2. A respiration system in accordance with claim 1, wherein the mass $m_{valve}$ of the valve body is selected such that $$m_{valve} > \frac{\sqrt{2} \cdot \pi^2 \cdot l_{supplyline2}^2 \cdot \dot{V}_{intersection} \cdot \rho_{gas}^2 \cdot d_{valve}^3 \cdot (\Delta P - \Delta P_{threshold})}{8 \cdot A_{supplyline2}^2 \cdot \Delta P^2 \cdot \sqrt{\frac{\rho_{gas}}{\Delta P}}}$$

applies, whereby $\dot{V}_{intersection} \geq 10$ L/min, $\Delta P = 5$ mbar and $\Delta P_{threshold} = 1.1$ mbar and a density $\rho_{gas}$ of a fluid in the respiration system is between 1.12 kg/m$^3$ and 2.19 kg/m$^3$.

3. A respiration system in accordance with claim 2, whereby $\dot{V}_{intersection} \geq 60$ L/min applies.

4. A respiration system in accordance with claim 1, wherein the reservoir is embodied as a flexible manual respiration bag with a variable volume.

5. A respiration system in accordance with claim 4, whereby the prestressing means comprises a coil spring lying against the valve body with a first end, which presses on the valve body against the effect of gravity and which is arranged on a side of the valve body pointing in the direction of the gravity.

6. A respiration system in accordance with claim 5, further comprising:
an adjusting screw mounted axially adjustably in the valve housing, wherein a second end of the coil spring is supported against the adjusting screw.

7. A respiration system in accordance with claim 1, wherein:
the anesthetic gas discharge valve has a valve housing, in which the valve seat is provided;
the valve seat extends in a seat plane running at right angles to the direction of gravity and points in a direction opposite the direction of gravity; and
the valve body is arranged such that it lies on valve seat under the effect of gravity.

8. A respiration system for feeding an anesthetic gas having a density $\rho_{gas}$, the system comprising:
a Y-piece for connection to a patient;
a respiration circuit with an inspiration branch and an expiration branch, which extend away from the Y-piece;
a branching in the expiration branch;
a reservoir;
a reservoir line connected from the branching and leading to the reservoir, said second supply line having a cross-sectional area $A_{supply\ line\ 2}$ and a length $l_{supply\ line\ 2}$;
an anesthetic gas discharge line connected from the branching;
an anesthetic gas discharge valve connected to the anesthetic gas discharge line, the anesthetic gas discharge valve comprises a circular-ring-shaped valve seat having a dimension, a valve body having a mass which is pressed, by means of the effect of gravity toward the circular-ring-shaped valve seat, the valve body being acted on by fluid pressure in the anesthetic gas discharge line in a direction against the effect of gravity and being acted on by atmospheric pressure in a direction of the effect of gravity and a prestressing means for exerting a prestressing force onto the valve body against the effect of gravity, so that the mass and the prestressing force determine a threshold pressure of the fluid pressure in the anesthetic gas discharge line that results in an opening of the anesthetic gas discharge valve.

9. A respiration system in accordance with claim 8, wherein the mass $m_{valve}$ of the valve body is selected such that $$m_{valve} > \frac{\sqrt{2} \cdot \pi^2 \cdot l_{supplyline2}^2 \cdot \dot{V}_{intersection} \cdot \rho_{gas}^2 \cdot d_{valve}^3 \cdot (\Delta P - \Delta P_{threshold})}{8 \cdot A_{supplyline2}^2 \cdot \Delta P^2 \cdot \sqrt{\frac{\rho_{gas}}{\Delta P}}}$$

wherein $A_{supply\ line\ 2}$ is a cross-sectional area of said second supply line and $l_{supply\ line\ 2}$ is a length of said second supply line and $\dot{V}_{intersection} \geq 10$ L/min, $\Delta P = 5$ mbar and $\Delta P_{threshold} = 1.1$ mbar and a density $\rho_{gas}$ of a fluid in the respiration system is between 1.12 kg/m$^3$ and 2.19 kg/m$^3$.

10. A respiration system in accordance with claim 9, whereby $\dot{V}_{intersection} \geq 60$ L/min.

11. A respiration system in accordance with claim 8, wherein the reservoir is embodied as a flexible manual respiration bag with a variable volume.

12. A respiration system in accordance with claim 8, wherein:
the anesthetic gas discharge valve has a valve housing, in which the valve seat is provided;
the valve seat extends in a seat plane running at right angles to the direction of gravity and points in a direction opposite the direction of gravity; and
the valve body is arranged such that it lies on valve seat under the effect of gravity.

13. A respiration system in accordance with claim 12, whereby said prestressing means comprises a coil spring lying against the valve body with a first end, which presses on the valve body against the effect of gravity and which is arranged on a side of the valve body pointing in the direction of the gravity.

14. A respiration system in accordance with claim 13, further comprising:
an adjusting screw mounted axially adjustably in the valve housing, wherein a second end of the coil spring is supported against the adjusting screw.

15. A respiration system for feeding an anesthetic gas having a density $\rho_{gas}$, the system comprising:
a Y-piece for connection to a patient;
a respiration circuit with an inspiration branch and an expiration branch, which extend away from the Y-piece;
a branching in the expiration branch;
a reservoir;
a reservoir line connected from the branching and leading to the reservoir, said second supply line having a cross-sectional area $A_{supply\ line\ 2}$ and a length $l_{supply\ line\ 2}$;
an anesthetic gas discharge line connected from the branching;
an anesthetic gas discharge valve connected to the anesthetic gas discharge line, said anesthetic gas discharge valve comprising a circular-ring-shaped valve seat having a dimension, a valve body having a mass which is pressed, by means of the effect of gravity toward the circular-ring-shaped valve seat, the valve body being acted on by fluid pressure in the anesthetic gas discharge line in a direction against the effect of gravity and being acted on by atmospheric pressure in a direction of the effect of gravity and a prestressing means for exerting a prestressing force onto the valve body against the effect of gravity, so that the mass and the prestressing force determine a threshold pressure of the fluid pressure in the anesthetic gas discharge line that results in an opening of the anesthetic gas discharge valve, said valve body having a valve body surface facing in the direction of the effect of gravity, said prestressing means engaging said valve body surface.

16. A respiration system in accordance with claim 15, wherein said threshold pressure is exclusively defined by said mass of said valve body and said prestressing force.

17. A respiration system in accordance with claim 15, wherein the mass $m_{valve}$ of the valve body is selected such that $$m_{valve} > \frac{\sqrt{2} \cdot \pi^2 \cdot l_{supplyline2}^2 \cdot \dot{V}_{intersection} \cdot \rho_{gas}^2 \cdot d_{valve}^3 \cdot (\Delta P - \Delta P_{threshold})}{8 \cdot A_{supplyline2}^2 \cdot \Delta P^2 \cdot \sqrt{\frac{\rho_{gas}}{\Delta P}}}$$

applies, whereby $\dot{V}_{intersection} \geq 10$ L/min, $\Delta P=5$ mbar and $\Delta P_{threshold}=1.1$ mbar and a density $\rho_{gas}$ of a fluid in the respiration system is between 1.12 kg/m$^3$ and 2.19 kg/m$^3$, d corresponding to a diameter of the valve body, wherein the diameter of the valve body, the cross-sectional area $A_{supply\ line\ 2}$ and the length $l_{supply\ line\ 2}$ are greater than zero.

18. A respiration system in accordance with claim 17, whereby $\dot{V}_{intersection} \geq 60$ L/min applies.

19. A respiration system in accordance with claim 15, wherein the reservoir is embodied as a flexible manual respiration bag with a variable volume.

20. A respiration system in accordance with claim 15, wherein:
   the anesthetic gas discharge valve has a valve housing, in which the valve seat is provided;
   the valve seat extends in a seat plane running at right angles to the direction of gravity and points in a direction opposite the direction of gravity; and
   the valve body is arranged such that it lies on valve seat under the effect of gravity.

* * * * *